United States Patent
Nagale et al.

(10) Patent No.: US 9,265,459 B2
(45) Date of Patent: *Feb. 23, 2016

(54) METHODS AND SYSTEMS FOR DETECTION AND THERMAL TREATMENT OF LOWER URINARY TRACT CONDITIONS

(71) Applicant: Boston Scientific Scimed, Inc., Maple Grove, MN (US)

(72) Inventors: Sandra Nagale, Lowell, MA (US); Ruth Cheng, Natick, MA (US); John Sherry, Needham, MA (US); David Borzelleca, Hudson, MA (US)

( * ) Notice: Subject to any disclaimer, the term of this patent is extended or adjusted under 35 U.S.C. 154(b) by 88 days.

This patent is subject to a terminal disclaimer.

(21) Appl. No.: 13/646,332

(22) Filed: Oct. 5, 2012

(65) Prior Publication Data

US 2013/0090648 A1   Apr. 11, 2013

Related U.S. Application Data

(60) Provisional application No. 61/544,878, filed on Oct. 7, 2011, provisional application No. 61/618,421, filed on Mar. 30, 2012.

(51) Int. Cl.
*A61B 18/20* (2006.01)
*A61B 18/18* (2006.01)
(Continued)

(52) U.S. Cl.
CPC ............. *A61B 5/202* (2013.01); *A61B 5/6852* (2013.01); *A61B 5/6874* (2013.01); *A61B 18/1485* (2013.01); *A61B 18/1492* (2013.01); *A61B 18/18* (2013.01); *A61B 18/1815* (2013.01); *A61B 18/20* (2013.01); *A61B 2017/00057* (2013.01); *A61B 2017/00075* (2013.01); *A61B 2018/00005* (2013.01); *A61B 2018/0016* (2013.01); *A61B 2018/0022* (2013.01); *A61B 2018/00047* (2013.01); *A61B 2018/00166* (2013.01); *A61B 2018/00214* (2013.01); *A61B 2018/00267* (2013.01); *A61B 2018/00517* (2013.01);
(Continued)

(58) Field of Classification Search
None
See application file for complete search history.

(56) References Cited

U.S. PATENT DOCUMENTS 5,127,077 A    6/1992   Iyer et al.
5,156,151 A *  10/1992  Imran .......................... 600/375
(Continued)

FOREIGN PATENT DOCUMENTS

WO   WO 2005/067791        7/2005
WO   WO 2012/083155 A2     6/2012

OTHER PUBLICATIONS

Partial International Search Report issued in PCT/US2012/059033, mailed Jan. 23, 2013. 2 pgs.
(Continued)

*Primary Examiner* — Lynsey Crandall
*Assistant Examiner* — Manolis Pahakis
(74) *Attorney, Agent, or Firm* — Bookoff McAndrews, PLLC

(57) ABSTRACT

The invention relates generally to systems and methods for detecting and/or treating lower urinary tract conditions. One embodiment of the invention is directed to a medical device. The medical device includes an elongate member having a proximal end and a distal end and an end effector assembly that extends distally from the distal end of the elongate member. The end effector assembly includes a plurality of end effector units. Each end effector unit has a sensing element for detecting a location of abnormal organ function and a treatment element for treating the location of abnormal organ function.

11 Claims, 7 Drawing Sheets

(51) Int. Cl.
*A61B 5/20* (2006.01)
*A61B 5/00* (2006.01)
*A61B 18/14* (2006.01)
*A61N 7/00* (2006.01)
*A61B 17/00* (2006.01)
*A61B 18/00* (2006.01)
*A61B 18/02* (2006.01)

(52) U.S. Cl.
CPC ............... *A61B2018/00642* (2013.01); *A61B 2018/00839* (2013.01); *A61B 2018/0212* (2013.01); *A61N 7/00* (2013.01)

(56) References Cited

U.S. PATENT DOCUMENTS

| | | | |
|---|---|---|---|
| 5,261,889 A * | 11/1993 | Laine et al. | 604/164.11 |
| 5,277,201 A * | 1/1994 | Stern | 607/98 |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A * | 6/1994 | Imran | 606/15 |
| 5,345,936 A * | 9/1994 | Pomeranz et al. | 600/374 |
| 5,348,554 A * | 9/1994 | Imran et al. | 606/41 |
| 5,366,490 A | 11/1994 | Edwards et al. | |
| 5,370,675 A | 12/1994 | Edwards et al. | |
| 5,435,805 A * | 7/1995 | Edwards et al. | 604/22 |
| 5,471,982 A | 12/1995 | Edwards | |
| 5,486,161 A * | 1/1996 | Lax et al. | 604/22 |
| 5,545,171 A | 8/1996 | Sharkey et al. | |
| 5,545,193 A | 8/1996 | Fleischman et al. | |
| 5,588,960 A * | 12/1996 | Edwards et al. | 604/20 |
| 5,617,876 A | 4/1997 | Van Duyl | |
| 5,636,634 A * | 6/1997 | Kordis et al. | 600/534 |
| 5,662,108 A | 9/1997 | Budd et al. | |
| 5,704,353 A * | 1/1998 | Kalb et al. | 600/342 |
| 5,706,809 A | 1/1998 | Littmann et al. | |
| RE35,880 E | 8/1998 | Waldman et al. | |
| 5,836,874 A * | 11/1998 | Swanson et al. | 600/374 |
| 5,849,011 A * | 12/1998 | Jones et al. | 606/47 |
| 5,860,974 A * | 1/1999 | Abele | 606/41 |
| 5,893,885 A * | 4/1999 | Webster, Jr. | 607/122 |
| 5,961,513 A | 10/1999 | Swanson et al. | |
| 5,964,796 A * | 10/1999 | Imran | 607/122 |
| 6,006,755 A * | 12/1999 | Edwards | 128/898 |
| 6,009,877 A * | 1/2000 | Edwards | 128/898 |
| 6,014,579 A * | 1/2000 | Pomeranz et al. | 600/374 |
| 6,038,472 A * | 3/2000 | Williams et al. | 607/5 |
| 6,056,744 A | 5/2000 | Edwards | |
| 6,073,052 A * | 6/2000 | Zelickson et al. | 607/100 |
| 6,088,610 A * | 7/2000 | Littmann et al. | 600/381 |
| 6,115,626 A | 9/2000 | Whayne et al. | |
| 6,156,029 A * | 12/2000 | Mueller | 606/7 |
| 6,296,608 B1 * | 10/2001 | Daniels et al. | 600/104 |
| 6,416,505 B1 | 7/2002 | Fleischman et al. | |
| 6,463,331 B1 * | 10/2002 | Edwards | 607/101 |
| 6,571,127 B1 | 5/2003 | Ben-Haim et al. | |
| 6,645,201 B1 | 11/2003 | Utley et al. | |
| 6,660,003 B1 * | 12/2003 | DeVore et al. | 606/45 |
| 6,673,070 B2 | 1/2004 | Edwards et al. | |
| 6,692,490 B1 * | 2/2004 | Edwards | 606/41 |
| 6,994,704 B2 | 2/2006 | Qin et al. | |
| 7,022,105 B1 * | 4/2006 | Edwards | 604/103.01 |
| 7,056,320 B2 | 6/2006 | Utley | |
| 7,125,407 B2 * | 10/2006 | Edwards et al. | 606/41 |
| 7,165,551 B2 * | 1/2007 | Edwards et al. | 128/898 |
| 7,326,235 B2 | 2/2008 | Edwards | |
| 7,615,014 B2 | 11/2009 | Omata et al. | |
| 7,648,500 B2 | 1/2010 | Edwards et al. | |
| 7,742,795 B2 | 6/2010 | Stone et al. | |
| 7,850,685 B2 | 12/2010 | Kunis et al. | |
| 8,177,781 B2 * | 5/2012 | Thomas et al. | 606/27 |
| 8,672,923 B2 | 3/2014 | Ladtkow et al. | |
| 2001/0009976 A1 | 7/2001 | Panescu et al. | |
| 2002/0013581 A1 | 1/2002 | Edwards et al. | |
| 2002/0026188 A1 * | 2/2002 | Balbierz et al. | 606/41 |
| 2002/0072742 A1 * | 6/2002 | Schaefer et al. | 606/41 |
| 2003/0055307 A1 | 3/2003 | Elmaleh et al. | |
| 2003/0212394 A1 * | 11/2003 | Pearson et al. | 606/41 |
| 2004/0068203 A1 | 4/2004 | Gellman et al. | |
| 2004/0153058 A1 | 8/2004 | West et al. | |
| 2004/0176755 A1 | 9/2004 | Lafontaine | |
| 2006/0173359 A1 * | 8/2006 | Lin et al. | 600/478 |
| 2007/0282184 A1 * | 12/2007 | Roberts | 600/345 |
| 2008/0009747 A1 | 1/2008 | Saadat et al. | |
| 2008/0015569 A1 | 1/2008 | Saadat et al. | |
| 2008/0215040 A1 | 9/2008 | Paithankar et al. | |
| 2010/0166739 A1 | 7/2010 | Chancellor et al. | |
| 2012/0265198 A1 * | 10/2012 | Crow et al. | 606/41 |
| 2013/0018281 A1 * | 1/2013 | Nagale et al. | 600/587 |
| 2013/0035576 A1 | 2/2013 | O'Grady et al. | |
| 2013/0090640 A1 | 4/2013 | Nagale et al. | |

OTHER PUBLICATIONS

R.G. Charlton, et al., "Focal changes in nerve, muscle and connective tissue in normal and unstable human bladder," BJU International (1999) vol. 84, pp. 953-960.

Alexander Roosen, et al., Voiding Dysfunction, "Characteristics of Spontaneous Activity in the Bladder Trigone," European Association of Urology (EAU), European Urology (2009), vol. 54, pp. 346-354.

M.J. Drake, et al., Hypothesis, "Model of peripheral autonomous modules and a myovesical plexus in normal and overactive bladder function," The Lancet (Aug. 4, 2001), vol. 358, pp. 401-403.

Seham M. D. Mustafa et al., "Cooling-induced bladder contraction: Studies on isolated detrusor muscle preparations in the rat," Urology (1999) vol. 53 (3), pp. 653-657.

T. Hague et al., "The effect of heating (37-41 degrees C) on detrusor contractile function in rabbit mucosa-intact and denuded preparations," Neurology and Urodynamics, Beijing, Peoples R China: $42^{nd}$ Annual Meeting of International Continence Society (ICS) vol. 31 (6), pp. 1027-1028.

T. Hague et al., "ICS 2012 Abstract Form, $42^{nd}$ Annual Meeting of the International Continence Society, Oct. 15-19, 2012, Beijing China", 2 pages.

Gulur, et al., "Management of Overactive Bladder," Nature Reviews/Urology, Oct. 2010, vol. 7, pp. 572-582.

Gillespie, et al., "On the Origins of the Sensory Output from the Bladder: the Concept of Afferent Noise," BJU International, 2009, vol. 103, pp. 1324-1333.

Kuo et al., "Novel Biomakers for Diagnosis and Therapeutic Assessment of Overactive Bladder: Urinary Nerve Growth Factor and Detrusor Wall Thickness," LUTS, 2009, pp. 559-561, 1.

Lemke et al., "Multisensor array for pH, $K^+$, $Na^+$ and $Ca^{2+}$ measurements based on coated-film electrodes," *Sensors and Actuators B*, 1992, pp. 488-491, 7.

Steers, William D., "Pathophysiology of Overactive Bladder and Urge Urinary Incontinence," Reviews in Urology, 2002, vol. 4, Suppl. 4, pp. S7-S18.

Partial International Search Report issued in PCT/US2012/059028, mailed Jan. 23, 2013, 2 pgs.

* cited by examiner

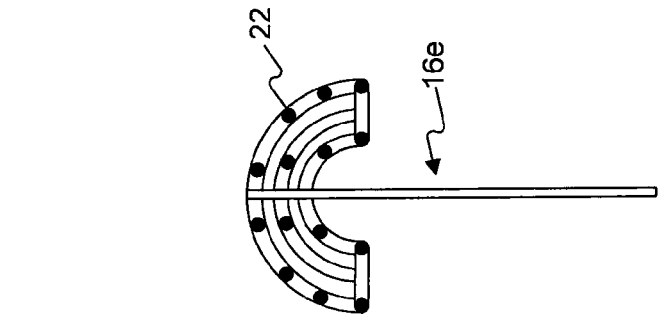
FIG. 5E
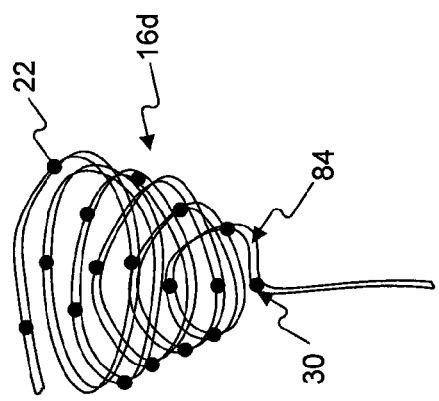
FIG. 5B
FIG. 5D
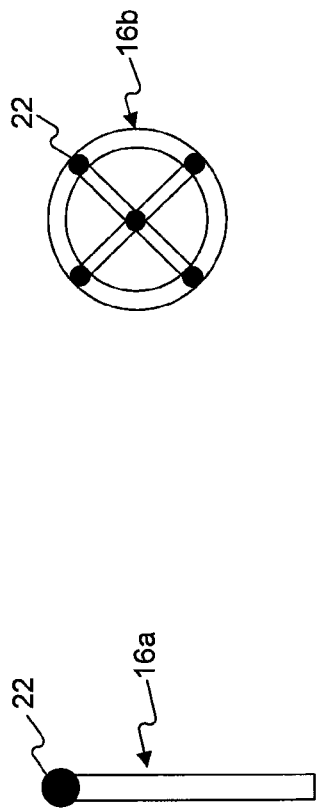
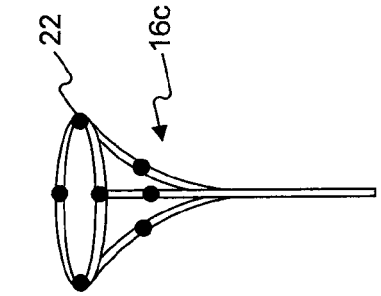
FIG. 5A
FIG. 5C

METHODS AND SYSTEMS FOR DETECTION AND THERMAL TREATMENT OF LOWER URINARY TRACT CONDITIONS

CROSS-REFERENCE TO RELATED APPLICATIONS

This application claims the benefit of priority from U.S. Provisional Application No. 61/544,878, filed Oct. 7, 2011, and U.S. Provisional Application No. 61/618,421, filed Mar. 30, 2012, the entirety of all of which are incorporated herein by reference.

FIELD OF THE INVENTION

Embodiments of the invention relate generally to systems and methods for detecting and/or treating lower urinary tract conditions. More particularly, embodiments of the invention relate to systems and methods for detecting and/or treating bladder overactivity.

BACKGROUND OF THE INVENTION

Overactive bladder is characterized by involuntary contractions of the detrusor muscle during bladder filling, which result in a sudden urge to urinate. The urge may be difficult to suppress, and can lead to involuntary loss of urine. Clinical manifestations of detrusor instability include urinary frequency, urinary urgency, and urinary urge incontinence.

Though little is known about the mechanisms underlying detrusor instability, recent studies suggest that the abnormal activity of the detrusor muscle may be a consequence of changes in the morphology and physiological or biochemical function of nerve, muscle, and connective tissues. These changes likely originate from defects on the cellular level or from changes in the nervous system. See M. J. Drake et al., *Model of peripheral autonomous modules and a myovesical plexus in normal and overactive bladder function*, 350 The Lancet 401, 401-403 (2001). Morphological studies show that changes to the nerve, muscle, and connective tissues are not uniform in idiopathic and neuropathic bladders. Instead, discrete areas of connective tissue infiltration, muscle hypertrophy, and altered innervations have been observed. See R. G. Charlton et al., *Focal changes in nerve, muscle and connective tissue in normal and unstable human bladder*, 84 BJU Int. 953, 953-960 (1999). These localized changes in the morphology of bladder tissue may contribute to abnormal function of the detrusor muscle on a macroscopic scale.

Moreover, studies suggest that the abnormal activity of the detrusor muscle may originate from one or more distinct anatomical areas of the bladder. For example, the abnormal activity of the detrusor muscle may originate in either the bladder dome or the internal sphincter, resulting in the dyssynchronous function of the entire bladder. In some instances, abnormal activity of the detrusor muscle may originate in the trigone. Evidence of cellular communication between the trigone and the detrusor muscle suggests that spontaneous activity of the trigone may be a precursor to bladder overactivity. See A. Roosen et al., *Characteristics of Spontaneous Activity in the Bladder Trigone*, 56 European Urology 346, 346-354 (2009).

Current methods to treat bladder overactivity include systemic drugs, nerve stimulation, and electrical stimulation. These known methods target the function of the entire bladder and do not address local changes and activity originating at specific anatomical areas of the bladder. Therefore, a need exists for methods and systems capable of both identifying and/or delivering therapy to specific anatomical areas of the bladder.

SUMMARY OF THE INVENTION

Embodiments of the present invention are directed to systems and methods for detecting and/or treating lower urinary tract conditions that obviate one or more of the limitations and disadvantages of known methods.

One embodiment of the invention is directed to a medical device. The medical device may include an elongate member having a proximal end and a distal end and an end effector assembly that extends distally from the distal end of the elongate member. The end effector assembly may include a plurality of end effector units. Each end effector unit may have a sensing element for detecting a location of abnormal organ function and a treatment element for treating the location of abnormal organ function.

In various embodiments, the medical device may include one or more of the following additional features: wherein the end effector assembly includes a plurality of legs extending from a proximal end of the end effector assembly to a distal end of the end effector assembly, the plurality of legs forming a three-dimensional sphere in an expanded state; wherein each leg includes a plurality of lumens, and wherein each lumen is in communication with a corresponding lumen of the elongate member; wherein each lumen of each leg of the end effector assembly and corresponding lumen of the elongate member receives a bundle that terminates at one of the plurality of end effectors; wherein the bundle includes a wire, a fluid conduit, a lead, a catheter, and an optical fiber; wherein the plurality of end effector units are substantially uniformly disposed on the end effector assembly; wherein each end effector unit further includes a second treatment element for treating the location of abnormal organ function; and wherein each end effector unit further includes a fluid conduit for delivering a fluid to the location of abnormal organ function.

Another embodiment of the invention is directed to a device for treating a lower urinary tract condition. The device may include an elongate member having a proximal end, a distal end, and one or more lumens. The device may also include an end effector assembly extending distally from the distal end of the elongate member. The end effector assembly may define one or more exit apertures. Each exit aperture may be in communication with a corresponding lumen of the elongate member. The device may also include one or more bundles. Each bundle may extend through one of the one or more lumens of the elongate member and terminate at an end effector unit disposed in one of the one or more exit apertures.

In various embodiments, the system may include one or more of the following additional features: wherein the end effector unit is configured to contact tissue; wherein the end effector unit includes one or more apertures and a fluid port; wherein each bundle includes a wire that terminates at a sensing device provided in one of the one or more apertures of the end effector unit; wherein each bundle includes an energy transmission medium that terminates at a treatment element provided in another of the one or more apertures of the end effector unit; and wherein the treatment element is adjacent a distal facing surface of the end effector unit; and wherein each bundle includes a fluid conduit that terminates at the fluid port.

Yet another embodiment of the invention is directed to a method for treating a urinary system. The method may include inserting a medical device within an organ of the urinary system tract. The medical device may include an elongate member having a proximal end and a distal end and an end effector assembly extending distally from the distal end of the elongate member. The end effector assembly may include a plurality of end effector units each having a sensing element for detecting a location of abnormal function and a treatment element for treating the location of abnormal function. The method may further include positioning the medical device adjacent tissue of the organ of the urinary system and treating the location with the treatment element.

In various embodiments, the method may include one or more of the following additional features: further including detecting a location of abnormal function; contacting tissue with the plurality of end effector units; wherein the step of treating the location includes delivering energy through all of the end effector units; and further comprising delivering therapeutic fluids to tissue at the location treated with thermal energy.

Yet another embodiment of the invention is directed to a device for treating a lower urinary tract condition. The device may include a support structure configured to conform to a portion of a bladder; and a plurality of end effector units disposed on the support structure and in contact with the bladder, wherein the plurality of end effector units are configured to deliver thermal treatment to the bladder.

In various embodiments, the device may include wherein the support structure is formed of a plurality of filaments in an open mesh configuration; wherein the support structure is a continuous polymer sheet; wherein the plurality of end effector units are uniformly distributed on the support structure; wherein the end effector units are embedded in the support structure; wherein the support structure is configured to conform to be positioned on an outer surface of the bladder to deliver treatment to a selected portion of the bladder; and wherein the plurality of treatment elements include a first set of electrodes and a second set of electrodes configured to deliver energy when the first set of electrodes contact the second set of electrodes.

Yet another embodiment of the invention is directed to a method for treating a urinary system. The method may include inserting a medical device within the urinary system. The medical device may include a support structure configured to conform to a portion of a bladder; and a plurality of treatment elements disposed on the support structure for treating abnormal bladder function. The method may further include positioning the medical device adjacent tissue of the bladder; and delivering energy through the plurality of treatment elements as the bladder expands.

It is to be understood that both the foregoing general description and the following detailed description are exemplary and explanatory only and are not restrictive of the invention, as claimed.

BRIEF DESCRIPTION OF THE DRAWINGS

FIG. 5A-E illustrate alternative configurations of the end effector assembly of the medical device of FIG. 1, according to embodiments of the invention;

DESCRIPTION OF THE EMBODIMENTS

Reference will now be made in detail to exemplary embodiments of the invention, examples of which are illustrated in the accompanying drawings. Whenever possible, the same reference numbers will be used throughout the drawings to refer to same or like parts.

Embodiments of the invention relate generally to systems and methods for detecting and/or treating lower urinary tract conditions. More particularly, embodiments of the invention relate to systems and methods for detecting and/or treating bladder overactivity. Bladder overactivity is characterized by involuntary contractions of the detrusor muscle during bladder filling, which result in a sudden urge to urinate. The systems and methods described herein may be used to treat conditions of the body other than bladder overactivity such as, for example, bladder sphincter dyssynergia, stress incontinence, painful bladder syndrome (interstitial cystitis), nerve pain, hypertension, or arrhythmia.

Figure 1:
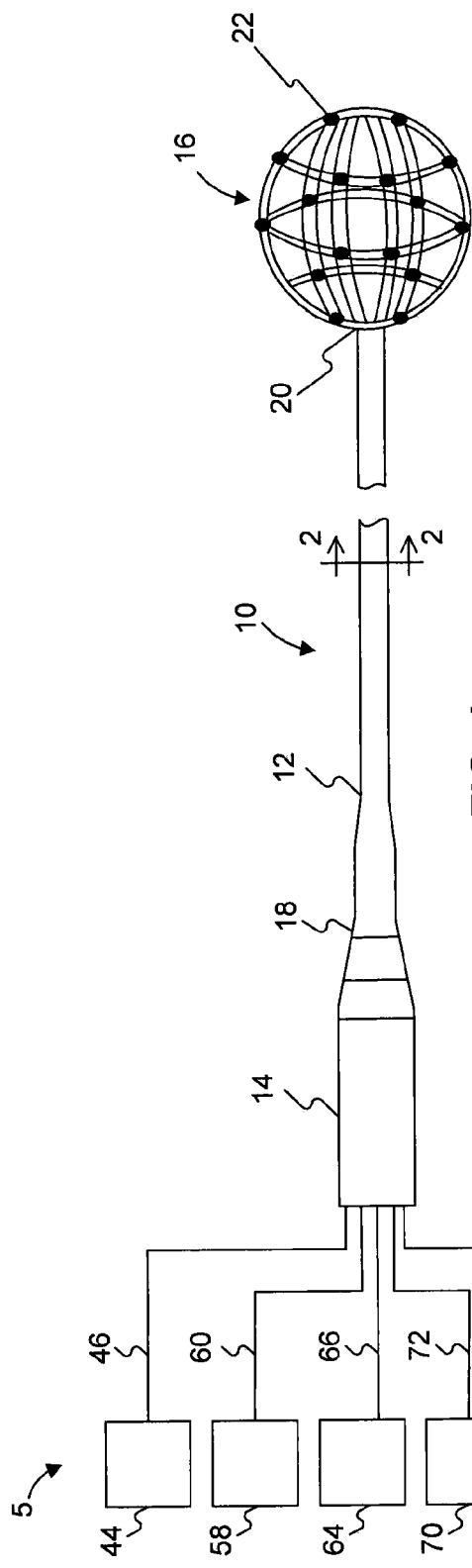
FIG. 1 illustrates a system for detecting and treating a urinary tract condition including a medical device having a plurality of end effector units, according to an embodiment of the invention.

FIG. 1 illustrates an exemplary system 5 including a medical device 10. In one embodiment, system 5 may include a fluid source 44 and one of a signal processing device 58, an electrical energy source 64, a coolant source 70, and a laser source 76. In another embodiment, system 5 may include fluid source 44 and two of: signal processing device 58, electrical energy source 64, a coolant source 70, and laser source 76. For example, system 5 may include fluid source 44, coolant source 70, and electrical energy source 64; or source 44, coolant source 70, and laser source 76. In yet another embodiment, system 5 may include fluid source 44, coolant source 70 and at least two of: signal processing device 58, electrical energy source 64, and laser source 76. Fluid source 44, signal processing device 58, electrical energy source 64, coolant source 70, and laser source 76 are connected to medical device 10 by way of one or more fluid conduits 46, leads 60, wires 66, catheters 72, and optical fibers 78, respectively. It is contemplated that additional cooling lines may be provided to provide temperature control.

Medical device 10 may include an elongate member 12, a handle portion 14, and an end effector assembly 16. Elongate member 12 may have a proximal end 18 and a distal end 20. For purposes of this disclosure, "proximal" refers to the end closer to the device operator during use, and "distal" refers to the end further from the device operator during use. Handle portion 14 may be disposed at proximal end 18 of elongate member 12 and end effector assembly 16 may be disposed at distal end 20 of elongate member 12. End effector assembly 16 may include one or more end effector units 22 uniformly distributed over end effector assembly 16 to detect abnormal bladder function and deliver therapeutic treatment to the bladder.

Figure 2:
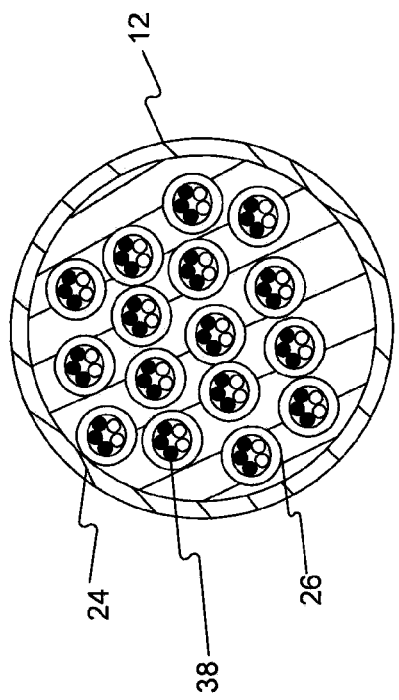
FIG. 2 is a cross-section of medical device along line 2-2 of FIG. 1.

FIG. 2 is a cross-section of elongate member 12 along lines 2-2 in FIG. 1. Elongate member 12 may be a solid rod or tube, made from any suitable biocompatible material known to one of ordinary skilled in the art having sufficient flexibility to traverse a urinary tract. Such materials may include, but are not limited to, rubber, silicon, synthetic plastics, stainless steel, metal-polymer composites, and metal alloys of nickel, titanium, copper cobalt, vanadium, chromium, and iron. In one embodiment, the material forming elongate member 12 may be a superelastic material such as nitinol, which is a nickel-titanium alloy. Elongate member 12 may have any cross-sectional shape and/or configuration and may be any desired dimension that can be received in the lower urinary tract. An outer sheath 24 may surround elongate member 12. Outer sheath may be constructed from an insulating polymer material such as polyamide, polyurethane, or any other suitable material.

Elongate member 12 may include one or more lumens 26 extending from proximal end 18 of the elongate member 12 to distal end 20 of the elongate member 12. It is to be understood that lumens 26 may have any size, cross-sectional area, shape, and/or configuration. Although the depicted embodiment includes sixteen lumens, elongate member 12 may include a greater or lesser number of lumens 26. It is to be understood that the number of lumens 26 may depend on the number of end effector units 22 on end effector assembly 16.

Figure 3A:
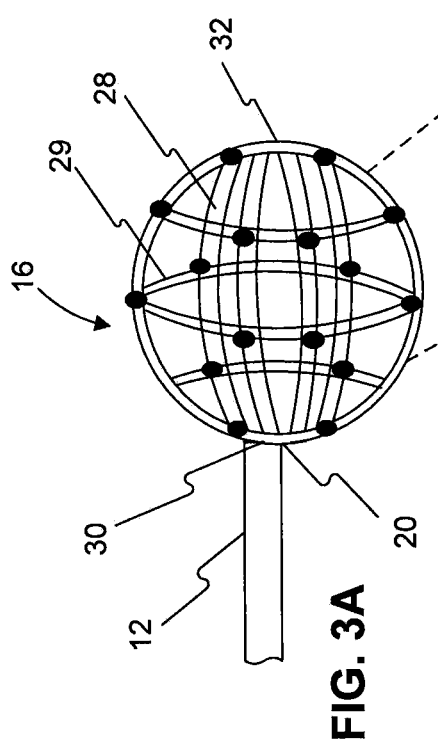
FIG. 3A is a side view of an end effector assembly of the medical device of FIG. 1, according to an embodiment of the invention.
Figure 3B:
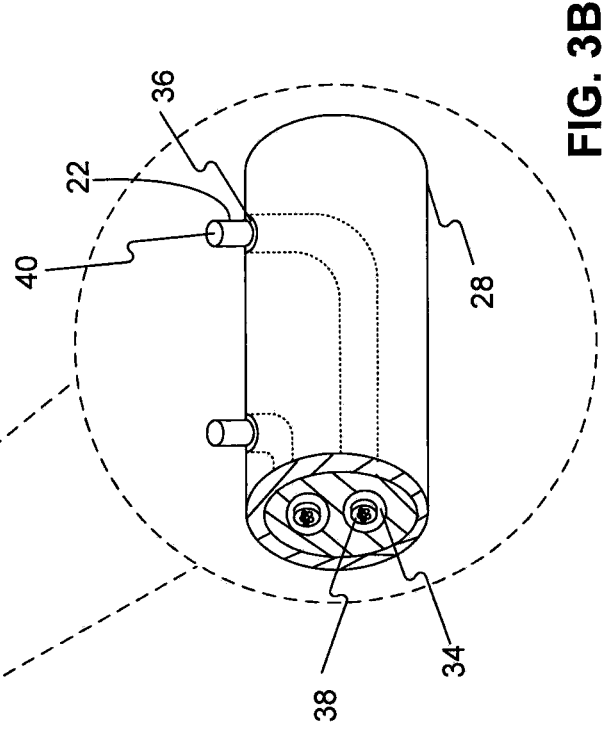
FIG. 3B is an exploded view of a portion of a leg of end effector assembly of FIG. 3A.

FIG. 3A depicts a side view of end effector assembly 16. As shown in FIG. 3A, end effector assembly 16 may extend distally from distal end 20 of elongate member 12, and may include a plurality of legs 28 extending from a proximal end 30 of end effector assembly 16 to a distal end 32 of end effector assembly 16. In some embodiments, end effector assembly 16 may also include one or more circumferentially extending legs, such as legs 29. In this disclosure, descriptions of legs 28 also pertain to legs 29, and vice versa.

End effector assembly 16 may be made out of the same piece of material as elongate member 12. Alternatively, end effector assembly 16 may be fabricated independently by any known means and may be made integral with elongate member 12 through connection of a proximal end 30 of the end effector assembly 16 to a region of elongate member 12, such as the distal end 20 of elongate member 12. Connection of proximal end 30 of end effector assembly 16 may be accomplished through any suitable means of fixedly connecting end effector assembly 16 to elongate member 12. For example, possible connections may include, but are not limited to welding, soldering, and/or crimping.

End effector assembly 16 may have any shape and/or configuration and may be any desired dimension that can be received in the lower urinary tract. In the exemplary embodiment shown in FIG. 3A, legs 28 are configured so that end effector assembly 16 forms a three-dimensional sphere in an expanded state. Legs 28 may be constructed from a material such as, for example, a shape memory metal alloy or a polymer material so that legs 28 may collapse to have a smaller cross-section in a collapsed state.

Although FIG. 3A, shows that that end effector assembly 16 comprises six legs 28 extending from proximal end 30 of end effector assembly 16 to a distal end 32 of end effector assembly 16 (and four circumferential legs 29), end effector assembly 16 may include any number of legs 28 (or 29) having any desired pattern and/or configuration. For example, legs 28 may be cylindrical, square, semi-circular, rectangular, or any other suitable shape. In addition, legs 28 may be any cross-sectional shape known in the art including, but not limited to, circular, square, or ovular.

Each leg 28 of end effector assembly 16 may include one or more lumens 34 located longitudinally therein. Lumens 34 may have any size, cross-sectional area, shape, and/or configuration. Each lumen 34 may be in communication with a corresponding lumen 26 of elongate member 12, and may extend from proximal end 30 of end effector assembly 20 to an exit aperture 36 on leg 28.

Within each lumen 26 of elongate member 12 and the corresponding lumen 34 of the end effector assembly 16 is a bundle of wires, optic fibers, and/or fluid conduits 38 that terminate at an individual end effector unit 22. More particularly, each bundle 38 may include one or more of a fluid conduit 46 associated with fluid source 44, at least one wire 60 associated with signal processing device 58, at least lead 66 associated with electrical energy source 64, at least one catheter 72 associated with coolant source 70, and at least one optical fiber 78 associated with laser source 76, that terminate at an individual end effector unit 22. The wires may be flexible circuits or polymer circuit wires having sufficient flexibility to traverse each lumen 26 and lumen 34. Each end effector unit 22 may be fixed in exit aperture 36 and extend outwardly from an exterior surface of leg 28. A surface 40 of each end effector unit 22 may be configured to contact tissue. In some embodiments, end-effector units 22 may have a conical shape a flat surface 40. In other embodiments, end effector units 22 may be tapered. Other shapes, sizes and/or configurations of end effector unit 22 and/or surface 40 are also contemplated. In some embodiments, each end effector unit may move relative to exit aperture 36. In those embodiments, each end effector unit may be a needle configured to penetrate tissue.

Figure 3C:
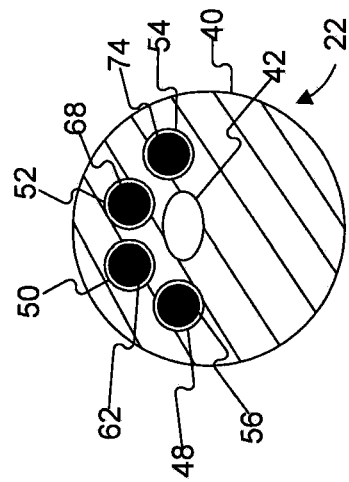
FIG. 3C is an end view of an individual end effector unit disposed on a leg of the distal assembly shown in FIG. 3B, according to an embodiment of the invention.

FIG. 3C is an end view of an individual end effector unit 22. As shown in FIG. 3C, each end effector unit 22 may include a fluid port 42. Fluid port 42 may have any size, shape, and/or configuration. Fluid port 42 may be configured to deliver therapeutic fluids from the fluid source 44 to tissue adjacent end effector unit 22. More particularly, fluid conduit 46 may extend from fluid port 42 of end effector unit 22 proximally through lumen 34 of leg 28 and a corresponding lumen 26 of elongate member 12 in bundle 38 to fluid source 44. With this arrangement, therapeutic, diagnostic, or other fluids may be circulated between fluid source 44 and fluid port 42 of end effector unit 22. Therapeutic fluids may include, for example, growth factors that promote tissue healing such as, for example, keratinocyte growth factor. Alternatively, the fluids may be an anti-infective agents or anesthetic.

Each end effector unit 22 may further include one or more apertures, separate from fluid port 42. In one embodiment, end effector unit 22 may include a first aperture 48, a second aperture 50, a third aperture 52, and a fourth aperture 54. Although the depicted embodiment of end effector unit 22 includes four apertures, end effector unit 22 may include a greater or lesser number of apertures. Apertures may have any size, shape, and/or configuration. For example, in the exemplary embodiment shown in FIG. 3C, each of first aperture 48, second aperture 50, third aperture 52, and fourth aperture 54 has a substantially circular cross-section.

A sensing element 56 may be provided in first aperture 48. Sensing element 56 may be flush with, or protrude from, surface 40 of end effector unit 22. Sensing element 56 may encompass physical, mechanical, chemical, electrical, and biochemical sensors, and may be of a type and kind well known in the art. Although the depicted embodiment includes a single sensing element 56, it is contemplated that a greater or lesser number of sensing elements 56 may be provided. It is further contemplated that in some embodiments, sensing element may be an imaging unit that, for example, includes a source for emitting light at a wavelength sufficient to induce fluorescence of tissue and sensors that are capable of detecting light at a wavelength at which tissue fluoresces.

Sensing element 56 may be configured to detect one or more indicators of abnormal bladder function such as, for example, abnormal detrusor contractions or excitability of a distinct anatomical area of the bladder. Sensing element 56 may transmit the measured information proximally to a signal processing device 58. More particularly, a wire 60 may extend from sensing element 56 proximally through lumen 34 of leg 28 and a corresponding lumen 26 of elongate member 12 in bundle 38 to signal processing device 56. Signal processing device 58 may be configured to process the information using methods and procedures known to one of ordinary skill in the art. Signal processing device 58 may be further configured to identify the location of abnormal bladder function and, more particularly, the site where the abnormal bladder function originates.

Treatment elements may be provided in each of second aperture 50, third aperture 52, and fourth aperture 54. Treatment elements may be fixed in each aperture 50, 52, and 54 or move relative to each aperture 50, 52, and 54. Treatment elements may be any suitable energy transmission medium known to one of ordinary skill in the art which operates by delivering energy such as, for example, thermal energy, microwave energy, radiofrequency energy, or laser energy, to a selected anatomical site to cause tissue necrosis. Such devices may include, but are not limited to, radio frequency (RF) devices, cryoablation catheters, lasers, microwave probes, needles, thermoelectric cooling devices, ultrasonic ablation devices, and other devices capable of heating or cooling tissue. In the preferred embodiment, an RF electrode 62 may be provided in second lumen 50, a cryoablation tip 68 may be provided in third aperture 52, and a distal end 74 of optical fiber 78 may be provided in fourth aperture 54. It is to be understood, however, that end effector unit 22 may include a greater or lesser number of treatment elements.

RF electrode 62 may be provided in second lumen 50 so that RF electrode 62 is flush with, or protrudes from, distal facing surface 40 of end effector unit 22. RF electrode 62 may be connected to an electrical energy source 64 (FIG. 1) such as, for example, an RF generator, to deliver electrical energy to tissue adjacent to end effector 22. More particularly, a wire 66 may extend from RF electrode 62 proximally through lumen 34 of leg 28 and corresponding lumen 26 of elongate member 12 in bundle 38 to electrical energy source 64. With this arrangement, RF energy can be transmitted from electrical energy source 64 to RF electrode 62.

Cryoablation tip 68 may be provided in third lumen 52 of end effector unit 22 such that cryoablation tip 68 is adjacent to, flush with, or protrudes from, distal facing surface 40 of end effector unit 22. Cryoablation tip 68 may be connected to a coolant source 70 (FIG. 1) so as to direct a flow of a coolant to distal surface 40 and remove heat from tissue adjacent to end effector 22. More particularly, a catheter 72 may extend from cryoablation tip 68 proximally through lumen 34 of leg 28 and corresponding lumen 26 of elongate member 12 in bundle 38 to coolant source 70. With this arrangement, coolant fluid may be circulated between coolant source 70 and cryoablation tip 68.

A distal end 74 of an optic fiber 78 may be provided in third lumen 54 of end effector unit 22 such that distal end 74 of optic fiber 78 is adjacent to, flush with, or protruding from distal facing surface 40 of end effector unit 22. Optic fiber 74 may be connected to a laser source 76 (FIG. 1) to deliver laser energy to tissue adjacent end effector 22. More particularly, optic fiber 74 may extend from end effector 22 proximally through lumen 34 of leg 28 and corresponding lumen 26 of elongate member 12 in bundle 38 to laser source 76. With this arrangement, laser energy can be transmitted from laser source 76 to distal end 74 of optic fiber 78.

In some additional embodiments, an imaging device (not shown) may be provided on each end effector unit 22. The imaging device may be a camera, lens, digital imaging chip (e.g., a CCD or CMOS chip), or other image receiving device. The imaging device may be connected to a control device (not shown) which may transmit signals using a fiber optic or another type of cable.

Figure 4B:
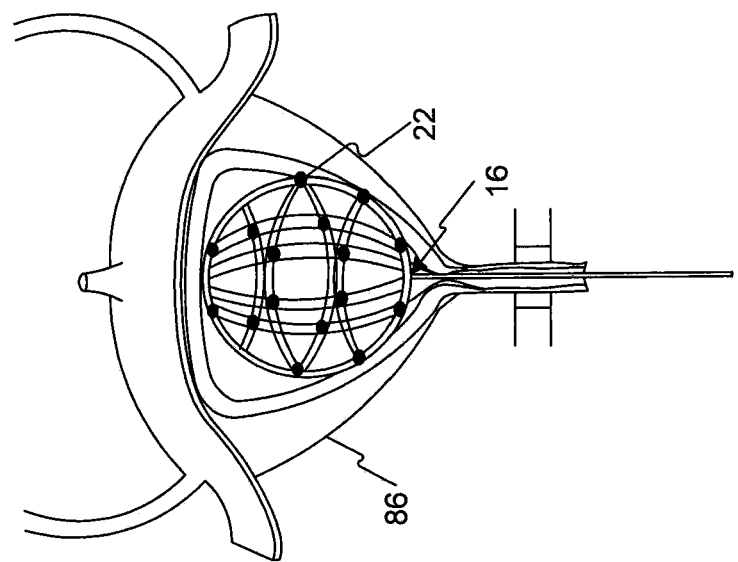
FIG. 4B illustrates a distal end of the medical device of FIG. 1 contacting an interior bladder wall to detect and/or treat abnormal bladder function, according to an embodiment of the invention.
Figure 4A:
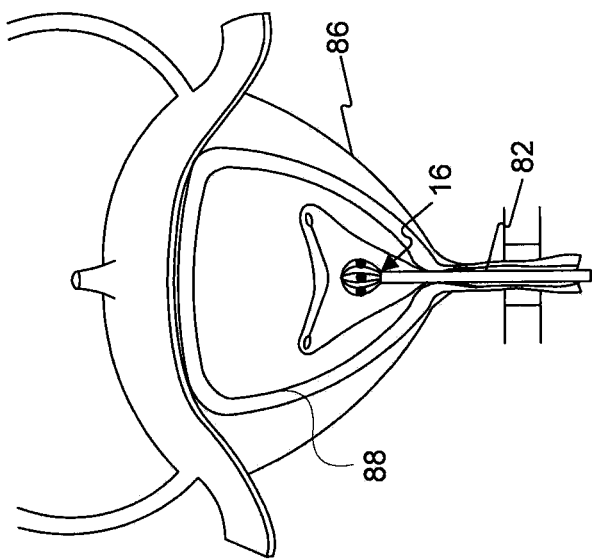
FIG. 4A illustrates a medical device being inserted into a bladder of a lower urinary tract of a body, according to an embodiment of the invention.

FIGS. 4A and 4B illustrate a method for detecting and/or treating a urinary tract condition such as, for example, bladder overactivity. Referring to FIG. 4A, medical device 10 may be inserted into the urethra of a patient for access to the internal sphincter, trigone, neck, or dome of a bladder 86. In some embodiments, when medical device 10 may be placed against an outer bladder wall, surgical access for placement against an outer bladder wall may be achieved using pelvic floor repair procedure or laparoscopic techniques. It is to be understood that, in addition to the bladder of the lower urinary tract, medical device 10 may be used in any visceral organ to detect and/or treat abnormal organ function.

It is contemplated that medical device 10 may be used for diagnostic and treatment purposes during a procedure. Alternatively, medical device 10 may be implanted temporarily or permanently within the bladder and end effector assembly 16 may communicate with a remote data processing unit wirelessly. For example, end effector assembly 16 may contain wireless sensing units configured to detect one or more indicators of abnormal bladder function and wireless treatment elements configured to delivery energy to the bladder (e.g., wireless RF electrode).

In one embodiment, medical device 10 may be advanced to bladder 86 through an access sheath 82. Once a distal end of access sheath is positioned in bladder 86, distal assembly 16 may be advanced distally out of sheath 82 so that distal assembly 16 may expand. For example, this may be achieved by pulling sheath 82 proximally relative to elongate member 12. Any suitable handle portion 18 may be used to effect deployment and expansion of end effector assembly 16. In an alternative embodiment, a balloon (not shown) may be placed in bladder 86 to distend bladder 86 so that end effector assembly 16 may expand. When fully expanded, end effector assembly 16 may have a substantially spherical shape such that surface 40 of each end effector unit 22 contacts an interior bladder wall 88 (FIG. 4B). It will be understood that end effector assembly 16 may have any other shape, size, and/or configuration.

In some embodiments, device operator may uniformly deliver energy to bladder 86 after positioning surfaces 40 of end effector units 22 adjacent to interior bladder wall 88. Energy may be delivered through the same treatment elements (i.e., RF electrode 62, cryoablation tip 68, distal end 74 of optic fiber 78, or any other temperature-controlled heating or cooling element) on each end effector unit 22 to uniformly treat tissue of bladder 86.

In other embodiments, sensing element 56 may be used to detect one or more indicators of abnormal bladder function. In one embodiment, each sensing element 56 may be configured to detect abnormal detrusor contractions. Additionally and/or alternatively, each sensing element 56 may be configured to detect the excitability of a distinct anatomical area of the bladder.

Each sensing element 56 may transmit the measured information to a signal processing device 58. Signal processing device 58 may then determine the origin of abnormal bladder function by methods and procedures known to one of ordinary skill in the art. In one embodiment, signal processing device 58 may map electrical activity of the bladder to determine the origin of abnormal bladder function.

After determining the location of the origin of abnormal bladder function, one or more treatment elements disposed on the end effector unit 22 located at the site at which abnormal bladder function originates may be activated to deliver energy to tissue adjacent the end effector unit 22. In some embodiments, the device operator may selectively deliver electrical energy through RF electrode 62 to tissue adjacent to end effector unit 22. The device operator may alternatively and/or additionally remove heat from tissue adjacent to end effector 22 through cryoablation tip 68. The device operator may alternatively and/or additionally deliver laser energy through distal end 74 of optic fiber 78 to tissue adjacent end effector unit 22.

Energy may be delivered at varying durations to achieve a range of effects from disrupting spontaneous detrusor contractions to inducing tissue shrinkage, collagen/elastin denaturation, or cellular necrosis. Additionally and/or alternatively, energy may be delivered at varying temperatures to effect cellular necrosis. For example, energy may be delivered at 55° C. and above to cause cell necrosis or at 45° C. to cause modification without necrosis. In other embodiments, energy may be delivered via cryoablation tip 68 below 37° C. for desired cell modification. The frequency, duration, and/or temperature of energy delivered to tissue adjacent end effector unit 22 may be determined based on the desired cell modification.

The therapy, including the form of energy delivered, frequency, duration, depth of ablation, and adjustment of temperature, may also be determined by the device operator based on the type of tissue at the site at which the abnormalities originate. For example, therapy may differ between treatment of skeletal muscle and treatment of smooth muscle cells. Additionally, therapy may be different for the treatment of the urothelium layer.

Therapeutic fluids may be delivered to the tissue adjacent end effector unit 22 after treatment. Therapeutic fluids may be delivered via fluid conduit 42 which may facilitate urothelial healing.

Alternative non-limiting examples of end effector assemblies having various shapes and/or distal configurations are shown in FIGS. 5A-5E.

FIGS. 5A and 5D depict end effector assemblies having wire configurations. In particular, end effector assembly 16b, as shown in FIG. 5A, may have a substantially linear configuration. A single end effector unit 22 may be disposed at distal end 32 of end effector assembly 16a. In another embodiment, end effector assembly 16d, as shown in FIG. 5D, may have a helical configuration preferably tapering from a larger diameter at a distalmost end thereof to a smaller diameter proximally of the distal-most end thereof. A kink 84 may be disposed adjacent proximal end 30 of end effector assembly 16d.

FIG. 5C depicts a medical device including end effector assembly 16c having a plurality of legs curving away from a longitudinal axis of end effector assembly 16c.

FIGS. 5B and 5E depict end effector assemblies having a mesh configuration. In particular, end effector assembly 16b, as shown in FIG. 5B, may have a circular shape. And in yet another embodiment, end effector assembly 16e, as shown in FIG. 5E, may have a semi-circular shape. End effector assemblies 16c and 16e may be additionally planar, concave, or convex.

Distal end configurations shown in FIGS. 1 and 5A-5E may facilitate placement of end effector units 22 at a selected anatomical area of the bladder or other organ. For example, in one embodiment, end effector assembly 16 as shown in FIG. 1 may facilitate placement adjacent an interior bladder wall 88. In another embodiment, end effector assemblies 16a and 16d, shown in FIGS. 5A and 5D, may facilitate placement in the internal sphincter. In yet another embodiment, end effector assemblies 16b and 16e, shown in FIGS. 5B and 5E, may facilitate placement adjacent the outer bladder wall. And in yet another embodiment, end effector assembly 16c may facilitate placement adjacent the trigone.

Figure 6:
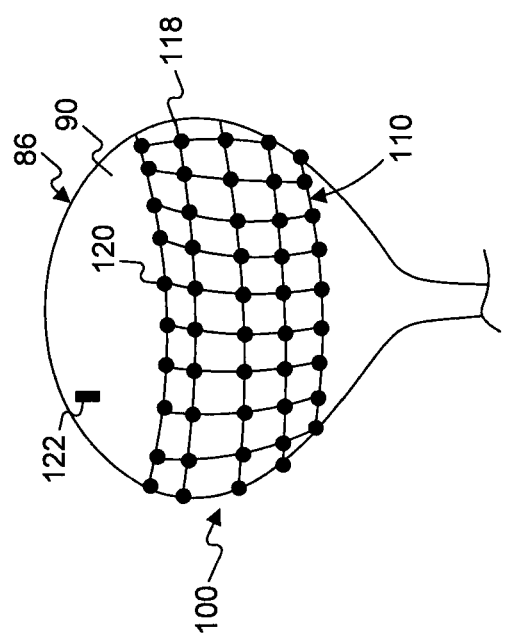
FIG. 6 illustrates a medical device positioned on an outer surface of a bladder wall, according to a second embodiment of the invention.

FIG. 6 depicts an exemplary medical device 100 and the components thereof in accordance with a second embodiment of the invention. As illustrated in FIG. 6, medical device 100 may include a support structure 110 and a plurality of treatment elements 120 substantially uniformly disposed on support structure 110 to deliver therapeutic treatment to bladder 86.

Support structure 110 may have any size, shape, and/or configuration capable of generally conforming to bladder 86. In the exemplary embodiment, support structure 110 may be a one-piece structure configured to extend completely around an outer surface of bladder wall 90 to surround a portion of bladder 86. It is contemplated, however, that support structure 110 may have any other size and/or configuration to conform to any other portion of bladder 86 including the interior of bladder 86. It is further contemplated that support structure 110 may not extend around the entire circumference of bladder 86, and may only extend around a portion of the circumference of bladder 86.

In one embodiment, support structure 110 may include a plurality of filaments 118 arranged in an open mesh configuration. Filaments 118 may be constructed from any suitable biocompatible material having elastic and recoil properties including, but not limited to, rubber, silk, synthetic plastics, stainless steel, metal-polymer composites, or metal alloys. In some embodiments, filaments 118 may be formed of conductive polymers or thermal conductive polymers configured to generate and apply heat to tissue of bladder 86 when supplied with electrical current. It is further contemplated that filaments 118 may be cast from conductive and non-conductive polymers so that selective portions of filaments 118 generate heat.

Filaments 118 may be designed so as to have sufficient flexibility and strength to maintain the position of support structure 110 on the outer surface bladder wall 90 and the relative position of treatment elements 120 as bladder 86 expands. Portions of filaments 118 may additionally and/or alternatively include adhesive materials so as to adhere support structure 110 to the outer surface of bladder wall 90. Other devices to retain support structure 110 on the outer surface of bladder wall 90 are also contemplated.

An array of treatment elements 120 may be attached to or embedded in support structure 110 so that treatment elements 120 are positioned adjacent bladder 86. In the exemplary embodiment illustrated in FIG. 6, treatment elements 120 are disposed at the intersection of filaments 118. While the depicted embodiment includes 50 treatment elements, it is contemplated that a greater or lesser number of treatment elements 120 may be provided. Treatment elements 120 may be any suitable energy transmission medium known to one of ordinary skill in the art which operates by delivering energy such as, for example, thermal energy, microwave energy, radiofrequency energy, or laser energy to treat tissue of bladder 86. Such devices may include, but are not limited to, radio frequency (RF) devices, lasers, microwave probes, ablation devices, and other devices capable of heating tissue.

In a preferred embodiment, treatment elements 120 may be electrodes. Electrodes may be connected to a source of electrical energy (not shown) to deliver thermal energy to bladder 86. In one embodiment, filaments 118 and a wire (not shown), may provide an electrical pathway from an energy source such as, for example, an implanted generator, to each treatment element 120. The generator may be implanted adjacent the scrotum, the buttocks, or within the abdominal musculature. In another exemplary embodiment, treatment elements 120 may wirelessly communicate with a source of electrical energy. In some embodiments, treatment elements 120 may be switchable electrodes. In these embodiments, treatment elements 120 may be activated to deliver thermal energy based on a sensed condition of bladder 86 such as, for example, bladder filling.

In other embodiments, treatment elements 120 may be optical elements. Optical elements may be connected to a source of energy to apply heat to the tissue of bladder 86. In one embodiment, filaments 118 may be optical fibers connected to a source of laser energy. In this embodiment, the treatment element may be the distal end of the optical fibers. In another embodiment, the optical elements may be LEDs directly or wirelessly connected to a source of electrical energy. In these embodiments, each optical element may be configured to deliver energy to the tissue of bladder 86 at a specific wavelength. Additionally and/or alternatively, the energy emitted from treatment elements 120 may be sufficient to activate a photothermal dye injected into the tissue of bladder 86. The photothermal dye may be, for example, chromophore chromophore palladium(II) octabutoxynaphthalocyanine (PdNc(OBu)8), or any other known photothermal dye.

A method of treating a urinary tract condition will now be described. Medical device 100 may be implanted temporarily or permanently in a patient having a urinary tract condition such as, for example, bladder overactivity. Support structure 110 of medical device 100 may be positioned on a portion of bladder wall 90 so as to conform to bladder 86. In the exemplary embodiment illustrated in FIG. 6, support structure 110 is positioned about the outer surface of bladder wall 90 to surround at least a portion of bladder 86. It is contemplated however, that support structure 110 may be positioned on any other surface including the interior surface of bladder 86. Surgical access for placement against bladder wall 90 may be achieved using pelvic floor repair procedure or laparoscopic techniques.

After positioning support structure 110 on bladder wall 90, treatment elements 120 may be configured to deliver energy to adjacent tissue of bladder 86. Treatment elements 120 may be coupled to an implanted generator or may be wireless units configured to be remotely activated to delivery energy.

Energy may be delivered through the array of treatment elements 120 to treat tissue of bladder 86. In some embodiments, treatment elements 120 may be configured to deliver energy based on a condition of bladder 86. A sensing element 122 may be provided to sense a condition such as, for example, the volume of fluid within bladder 86 or the pressure within bladder 86. Sensing element 122 may be combined with or separate from medical device 100, and may be a physical, chemical, electrical, or biochemical sensor, and may be of a type and kind well known in the art. Sensing element 122 may be configured to sense one or more physiological signals including but not limited to electrical activity, chemical signaling, or biological changes such as, for example, volume changes or pressure changes in the bladder. Sensing element 122 may transmit data relating to bladder conditions to an external device which may control activation of treatment elements 120. Treatment elements 120 may be activated to deliver energy uniformly to tissue of bladder 86 when the bladder 86 starts to fill, and may be configured to not deliver energy when bladder 86 is empty. In some embodiments, treatment elements 120 may be activated to deliver energy when bladder 86 reaches approximately 200-300 mL. After treatment elements 120 have been activated, treatment elements 120 may deliver energy continuously or periodically until bladder 86 has been emptied.

Additionally and/or alternatively, treatment elements 120 may be configured to deliver energy based on a location of the origin of abnormal function. In these embodiments, the same or a different sensing element may be configured to detect the excitability of a distinct anatomical area of the bladder (e.g., dome, trigone, interior bladder wall, exterior bladder wall, internal sphincter and/or ureter). After determining the location of the origin of abnormal bladder function, energy may be delivered through one or more selected treatment elements 120 to treat tissue at the origin of abnormal bladder function.

It is contemplated that the frequency, duration, and/or temperature of the energy applied to the tissue of bladder 86 may vary based the type of tissue at the treatment site. For example, therapy may differ between treatment of only the tissue cells, skeletal muscle cells, and smooth muscle cells. The therapy may also differ to treat different thicknesses of the bladder wall.

In some embodiments, it is contemplated that medical device 100 may be positioned adjacent outer bladder wall 90 and a second medical device 100 may be position adjacent an interior bladder wall to treat one or more anatomical sites of bladder 86.

Figure 7B:
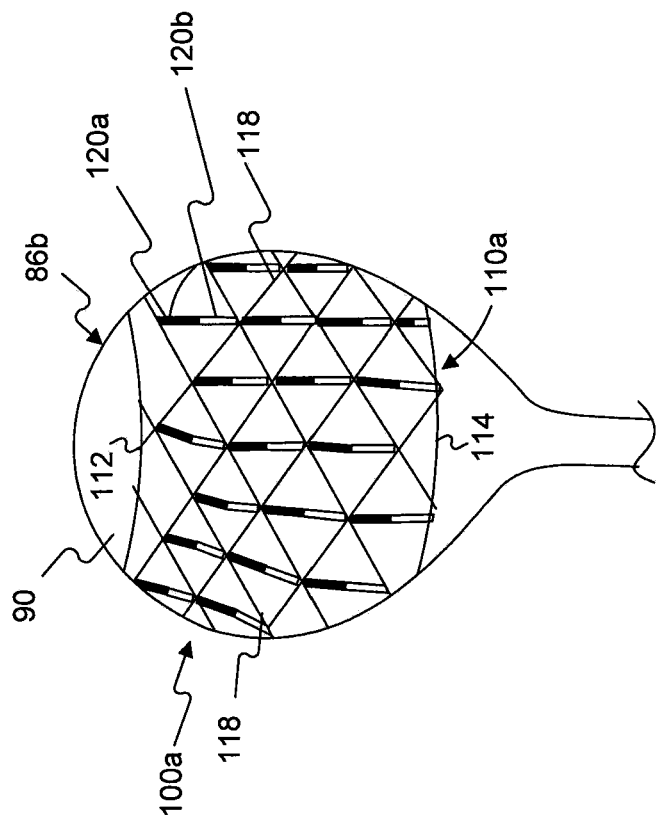
FIG. 7B illustrates an alternative embodiment of the medical device of FIG. 7A on an expanded bladder.
Figure 7A:
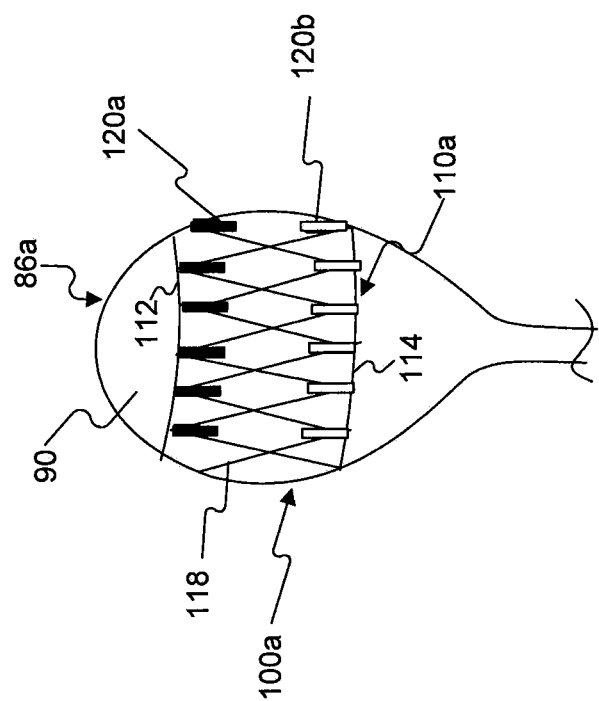
FIG. 7A illustrates an alternative embodiment of the medical device of FIG. 6 positioned on an empty bladder, the medical device includes a first set of treatment elements spaced from a second set of treatment elements.

FIG. 7A illustrates an alternative embodiment of the medical device shown in FIG. 6. In this embodiment, medical device 100a includes a support structure 110a having one or more filaments 118a extending between a first edge 112 and a second edge 114 of support structure 110a. Medical device 100 may also include a first set of treatment elements 120a and a second set of treatment elements 120b attached to or embedded in support structure 110a between first edge 112 and second edge 114. First set of treatment elements 120a and second set of treatment elements 120b may be conductive elements configured to deliver energy when first set of treatment elements 120a contact second set of treatment elements 120b. In some embodiments, first set of treatment elements and second set of treatment elements may be monopolar or bipolar electrodes. While the depicted embodiment illustrates a single row of the array, multiple rows are contemplated, as shown in FIG. 7B.

First set of treatment elements 120a and second set of treatment elements 120b may be positioned on filaments 118a so that first set of treatment elements 120a are spaced from second set of treatment elements 120b when bladder 86 is empty, as shown in FIG. 7A. As bladder 86 expands, filaments 118 may pivot relative to first edge 112 and second edge 114 to bring first edge 112 closer to second edge 114. In this manner, first set of treatment elements 120a are brought into contact with the second set of treatment elements 120*b*, as shown in FIG. 7B. Energy may be delivered through both the first set of treatment elements 120*a* and second set of treatment elements 120*b* when first set of treatment elements 120*a* contact second set of treatment elements 12*b* to treat tissue of bladder 86.

Figure 8:
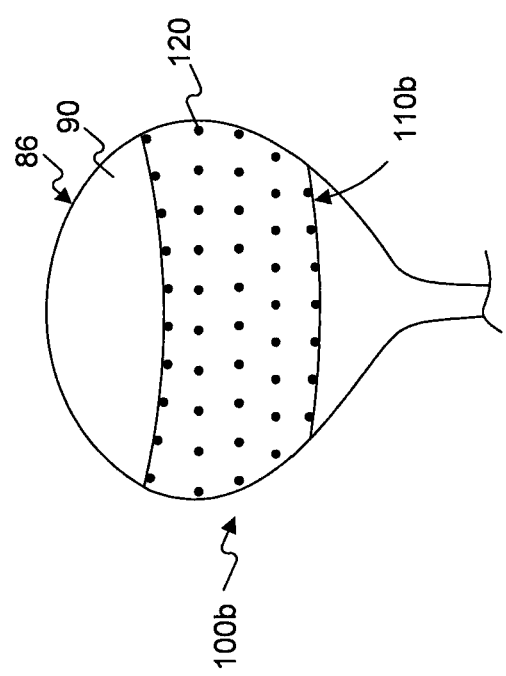
FIG. 8 illustrates another alternative embodiment of the medical device of FIG. 6.

Another embodiment of the medical device of FIG. 6 is shown in FIG. 8. In this embodiment, medical device 100*b* may include a support structure 110*b*. Support structure 110*b* may be, for example, a continuous or porous polymer sheet having an array of treatment elements 120 embedded therein. Support structure 110*b* may be constructed from flexible and/or elastic materials including, but are not limited to, elastomers, silicone, polytetrafluoroethylene (PTFE), polyethylene terephthalate (PET), fluorinated ethylene propylene (FEP), polypropylene, polyurethanes and their co-polymers, or thin films such as latex. In some embodiments, it is contemplated that the polymer sheet is constructed from conductive polymers and/or thermally conductive polymers that generate heat. Such polymers include, but are not limited to, ABS, nylon, liquid-crystal polymers (LCP), and polyetheretherketone (PEEK). In some embodiments, treatment elements 120 may be nanoparticle-sized electrodes embedded in support structure 110*b*. In other embodiments, support structure 110*b* may be a flexible circuit having treatment elements 120 formed therein. In these embodiments, treatment elements 120 may either be connected to a source of energy (e.g., implanted generator) or may be wirelessly in communication with a source of energy.

While the foregoing embodiments have been described individually, it is intended that disclosed medical devices may be used in combination for detecting and/or treating a urinary condition such as, for example, bladder overactivity. For example, medical device 100 may be position adjacent an outer surface of bladder wall 90 and medical device 10 may be positioned adjacent an interior surface of bladder wall 90 or vice versa to treat tissue located at various anatomical sites of bladder 86 and/or target various tissue layers.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
    an elongate member having a proximal end and a distal end;
    an end effector assembly extending distally from the distal end of the elongate member,
    wherein the end effector assembly includes a plurality of legs extending from a proximal end of the end effector assembly to a distal end of the end effector assembly, wherein each leg of the plurality of legs includes one or more leg lumens, each of the one or more leg lumens terminating in a corresponding leg aperture, wherein the plurality of legs form a sphere; and
    a plurality of bundles of elements, wherein each bundle of elements includes a sensor element configured to detect a location of abnormal organ function, a fluid conduit, and a plurality of energy transmission elements configured to treat the location of abnormal organ function, wherein each bundle of elements extends through the elongate member and through a leg lumen and terminates in an end effector unit, wherein the end effector unit extends through and is configured to move relative to a leg aperture, wherein each end effector unit has a distal end surface that forms a fluid port and a plurality of apertures configured to receive the sensor element and the plurality of energy transmission elements, wherein the fluid conduit terminates at the fluid port, and wherein the plurality of energy transmission elements are configured to move through the plurality of apertures and relative to the distal end surface of the end effector unit and the fluid port.

2. The medical device of claim 1, wherein the plurality of legs are collapsible and expandable and form the sphere in an expanded state.

3. The medical device of claim 1, wherein each leg lumen of the one or more leg lumens is in communication with a corresponding lumen of the elongate member.

4. The medical device of claim 1, wherein each bundle of elements includes at least two different energy transmission elements selected from an RF device, a cryoblation catheter, a laser, a microwave probe, a needle, a thermoelectric cooling device, and an ultrasonic ablation device.

5. The medical device of claim 1, wherein the plurality of end effector units corresponding to the plurality of bundles of elements are uniformly disposed on the end effector assembly.

6. The medical device of claim 1, further including a fluid source, a signal processing device, and an energy source selected from the group consisting of an RF generator, a coolant source, and a laser source.

7. A device for treating a lower urinary tract, comprising:
    an elongate member having a proximal end and a distal end;
    an end effector assembly extending distally from the distal end of the elongate member,
    wherein the end effector assembly includes a plurality of legs extending from a proximal end of the end effector assembly to a distal end of the end effector assembly, wherein each leg of the plurality of legs includes one or more leg lumens, each of the one or more leg lumens terminating in a corresponding leg aperture, wherein the plurality of legs form a sphere; and
    a plurality of bundles of elements, wherein each bundle of elements includes a sensor element configured to detect a location of abnormal bladder function, a fluid conduit, and a plurality of energy transmission elements configured to treat the location of abnormal bladder function, wherein the plurality of energy transmission elements are configured to transmit at least two different forms of energy selected from the group consisting of thermal energy, microwave energy, radiofrequency energy, or laser energy, wherein each bundle of elements extends through the elongate member and through a leg lumen and terminates in an end effector unit, wherein the end effector unit extends through and is configured to move relative to a leg aperture, wherein each end effector unit has a distal end surface that forms a fluid port and a plurality of apertures configured to receive the sensor element and the plurality of the energy transmission elements, wherein the fluid conduit terminates at the fluid port, and wherein the plurality of energy transmission elements are configured to move through the plurality of apertures and relative to the distal end surface of the end effector unit and the fluid port.

8. The medical device of claim 7, wherein each leg lumen of the one or more leg lumens is in communication with a corresponding lumen of the elongate member.

9. The medical device of claim 7, further including a fluid source, a signal processing device, and two energy sources selected from the group consisting of an RF generator, a coolant source, and a laser source.

10. The medical device of claim 7, wherein the plurality of end effector units corresponding to the plurality of bundles of elements are uniformly disposed on the end effector assembly.

11. The medical device of claim 7, wherein the end effector assembly is collapsible and expandable and forms the sphere in an expanded state.

* * * * *